(12) United States Patent
Sebree et al.

(10) Patent No.: US 9,327,114 B2
(45) Date of Patent: May 3, 2016

(54) USER-ACTIVATED SELF-CONTAINED CO-PACKAGED IONTOPHORETIC DRUG DELIVERY SYSTEM

(71) Applicant: Teva Pharmaceuticals International GmbH, Rapperseil-Jona OT (CH)

(72) Inventors: Terri B. Sebree, Gladwyne, PA (US); Robert P. Stathopulos, Boonton, NJ (US); Mihai A. Vinatoru, Graham, NC (US)

(73) Assignee: Teva Pharmaceuticals International GmbH, Rapperswil-Jona (CH)

( * ) Notice: Subject to any disclaimer, the term of this patent is extended or adjusted under 35 U.S.C. 154(b) by 334 days.

(21) Appl. No.: 13/802,156

(22) Filed: Mar. 13, 2013

(65) Prior Publication Data

US 2013/0296766 A1    Nov. 7, 2013

Related U.S. Application Data

(63) Continuation of application No. PCT/US2011/059981, filed on Nov. 9, 2011.

(60) Provisional application No. 61/416,623, filed on Nov. 23, 2010.

(51) Int. Cl.
*A61N 1/30* (2006.01)
*A61M 31/00* (2006.01)
*A61N 1/04* (2006.01)
*A61N 1/32* (2006.01)

(52) U.S. Cl.
CPC .............. *A61N 1/303* (2013.01); *A61N 1/0428* (2013.01); *A61N 1/325* (2013.01)

(58) Field of Classification Search
CPC ..... A61N 1/0428; A61N 1/303; A61N 1/325; A61N 1/0432; A61N 1/0444; A61N 1/0448; A61N 1/30; A61N 1/18; A61N 1/20; A61N 1/32
USPC .......................................................... 604/20
See application file for complete search history.

(56) References Cited

U.S. PATENT DOCUMENTS

| | | | |
|---|---|---|---|
| 4,141,359 | A | 2/1979 | Jacobsen et al. |
| 4,917,676 | A | 4/1990 | Heiber et al. |
| 5,042,975 | A | 8/1991 | Chien et al. |
| 5,047,007 | A | 9/1991 | McNichols et al. |
| 5,128,137 | A | 7/1992 | Muller et al. |

(Continued)

FOREIGN PATENT DOCUMENTS

| | | |
|---|---|---|
| EP | 0558409 A1 | 9/1993 |
| EP | 0847775 A1 | 6/1998 |

(Continued)

OTHER PUBLICATIONS

First Office Action issued by the State Intellectual Property Office for Chinese Patent Application No. 201180055905.3 on Aug. 12, 2014 (9 pages) with English Translation (10 pages).

(Continued)

*Primary Examiner* — Jason Flick
(74) *Attorney, Agent, or Firm* — McCarter & English, LLP; Danielle L. Herritt

(57) ABSTRACT

A user-activated self-contained co-packaged iontophoretic drug delivery system and method of use for treatment of a subject are described.

18 Claims, 6 Drawing Sheets

(56) References Cited

U.S. PATENT DOCUMENTS

| | | | |
|---|---|---|---|
| 5,246,418 A | 9/1993 | Haynes et al. | |
| 5,310,404 A * | 5/1994 | Gyory et al. | 604/20 |
| 5,426,387 A | 6/1995 | Teillaud et al. | |
| 5,445,609 A | 8/1995 | Lattin et al. | |
| 5,458,569 A | 10/1995 | Kirk, III et al. | |
| 5,499,967 A | 3/1996 | Teillaud et al. | |
| 5,662,925 A | 9/1997 | Ebert et al. | |
| 5,738,647 A | 4/1998 | Bernhard et al. | |
| 5,766,144 A | 6/1998 | Lai et al. | |
| 5,817,044 A | 10/1998 | Evers et al. | |
| 5,983,130 A | 11/1999 | Phipps et al. | |
| 6,035,234 A | 3/2000 | Riddle et al. | |
| 6,167,301 A | 12/2000 | Flower et al. | |
| 6,377,848 B1 | 4/2002 | Garde et al. | |
| 6,385,488 B1 | 5/2002 | Flower et al. | |
| 6,402,732 B1 | 6/2002 | Flower et al. | |
| 6,522,919 B1 | 2/2003 | Flower et al. | |
| 6,678,555 B2 | 1/2004 | Flower et al. | |
| 6,745,071 B1 | 6/2004 | Anderson et al. | |
| 6,842,640 B2 | 1/2005 | Riddle et al. | |
| 7,708,731 B2 | 5/2010 | Riddle et al. | |
| 7,937,141 B1 | 5/2011 | Inoue et al. | |
| 2001/0009983 A1 | 7/2001 | Walter et al. | |
| 2003/0013753 A1 | 1/2003 | Aung-Din | |
| 2008/0154179 A1 | 6/2008 | Cantor et al. | |
| 2009/0005824 A1 * | 1/2009 | Visco et al. | 607/3 |

FOREIGN PATENT DOCUMENTS

| | | |
|---|---|---|
| WO | 91/16943 A1 | 11/1991 |
| WO | 95/06497 A1 | 3/1995 |
| WO | 96/17651 A1 | 6/1996 |
| WO | 96/30077 A1 | 10/1996 |
| WO | 96/39223 A1 | 12/1996 |
| WO | 96/39224 A1 | 12/1996 |
| WO | 97/11743 A1 | 4/1997 |
| WO | 99/30773 A1 | 6/1999 |
| WO | 99/30775 A1 | 6/1999 |
| WO | 2010/078313 A1 | 7/2010 |
| WO | 2012/071175 A1 | 5/2012 |

OTHER PUBLICATIONS

International Preliminary Report on Patentability issued in International Application No. PCT/US2011/059981, issued May 28, 2013 (8 pages).
International Search Report and Written Opinion for Application No. PCT/US2011/059981, mailed on Mar. 7, 2012 (12 pages).
Notice of Reasons for Rejection issued in Japanese Patent Application No. 2013-539900, mailed Aug. 25, 2015.
Office Action issued in Eurasian Patent Application No. 201390745, dated Mar. 13, 2015 (2 pages) with English translation (2 pages).
Office Action issued in Mexican Patent Application No. MX/a/2013005430, dated May 18, 2015 (2 pages) with English translation (2 pages).
Patent Examination Report No. 1 issued by the Australian Patent Office for Patent Application No. 20011332187 on May 20, 2014 (3 pages).
Second Office Action issued by the State Intellectual Property Office for Chinese Patent Application No. 201180055905.3 on Apr. 24, 2015 (7 pages) with English translation (11 pages).
First Examination Report issued in New Zealand Patent Application No. 711148, dated Sep. 7, 2015 (3 pages).

* cited by examiner

USER-ACTIVATED SELF-CONTAINED CO-PACKAGED IONTOPHORETIC DRUG DELIVERY SYSTEM

REFERENCE TO RELATED APPLICATION

This application is a continuation of International Application Serial No. PCT/US2011/059981, filed Nov. 9, 2011, which claims priority to U.S. Provisional Application No. 61/416,623, filed on Nov. 23, 2010. The entire contents of each of these applications, including the specification, any drawings, and sequence listing, are incorporated herein by reference.

BACKGROUND OF THE INVENTION

Iontophoresis is a method of administration of a compound to a subject by applying a current to a subject's skin so that the compound is delivered transdermally to the subject through the subject's skin. Iontophoresis is often performed using iontophoresis devices such as patches and other devices which can be placed on the skin of a subject. Iontophoretic delivery of drugs is recognized as desirable, but it is not widely used because the devices that are commercially available do not, generally, meet the needs of the potential user population. Examples of such requirements include shelf-storage stability, reliability and ease of use.

SUMMARY OF THE INVENTION

The present invention provides a self-contained co-packaged iontophoretic drug delivery system. The iontophoretic drug delivery system includes a first electrode, a second electrode, a power controller (e.g., a power controller containing a microprocessor) configured to control a current flow between the first electrode and the second electrode, a first conductive reservoir holding a first conducting medium and a therapeutic compound, a second conductive reservoir holding a second conducting medium and optionally an ion source, a removable barrier forming a first barrier seal removably disposed between the first electrode and the first conductive reservoir, and a housing to house the first electrode, the first conductive reservoir, the second electrode, the second conductive reservoir and the power controller, the housing having a top housing portion coupleable to a bottom housing portion; wherein the top housing portion and the bottom housing portion are coupled to form a slotted sidewall portion thorough which the removable barrier extends.

In another aspect, the present invention provides a self-contained co-packaged iontophoretic drug delivery system. The iontophoretic drug delivery system of this embodiment includes an electrode region which comprises a first electrode and a return electrode, a power controller for controlling current supplied to the first electrode and the second electrode, circuitry connecting the first electrode and the second electrode with the power controller, a therapeutic compound region which comprises a first conductive medium vertically aligned with the first electrode, a second conductive medium vertically aligned with the second electrode, and a therapeutic compound in solution disposed in the first conductive medium; a protective housing substantially enclosing the electrode region and the therapeutic compound region; a removable barrier layer separating a portion of the electrode region from a portion of the therapeutic compound region, the removable barrier layer having a portion accessible from outside the housing; and wherein the removable bather layer is configured to be removed while the electrode region and the therapeutic compound remain within the housing; and wherein upon removal of the barrier layer, the first conductive medium adheres to the first electrode and makes electrical contact therewith, and the second conductive medium adheres to the second return electrode and makes electrical contact therewith.

In a further embodiment, the invention pertains, at least in part to a method of treating a subject using the iontophoretic drug delivery systems of the invention. In a further embodiment, the therapeutic compound, e.g., the drug delivered is a triptan, e.g., sumatriptan, and the subject is treated for a triptan responsive state, such as a migraine.

BRIEF DESCRIPTION OF THE DRAWINGS

These and other features and advantages of the mechanisms and methods disclosed herein will be more fully understood by reference to the following detailed description in conjunction with the attached drawings in which like reference numerals refer to like elements through the different views. The drawings illustrate principles of the instruments and methods disclosed herein and, although not to scale, show relative dimensions.

DETAILED DESCRIPTION OF THE INVENTION

Figure 1A:
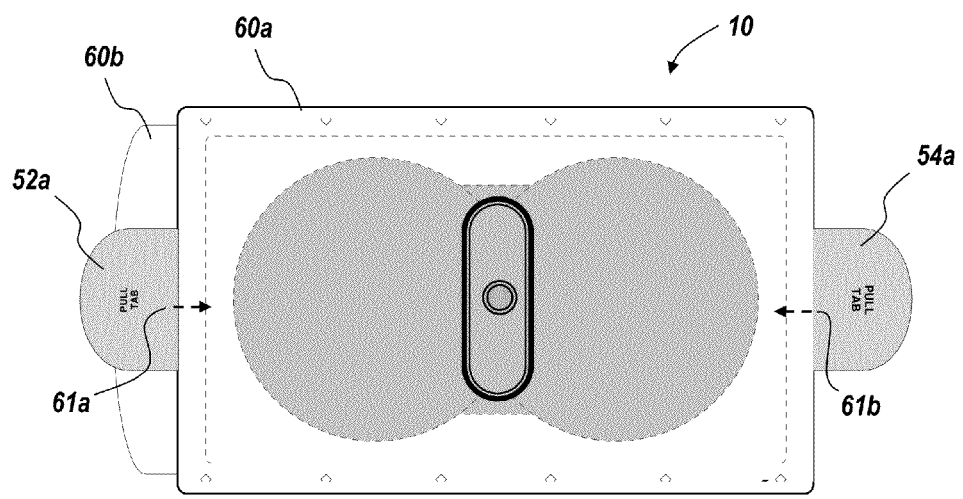
FIG. 1A illustrates a top view of an exemplary self-contained co-packaged iontophoretic drug delivery system that is user-activated, in accordance with an embodiment of the present invention.

Embodiments of the present invention include a self-contained co-packaged iontophoretic drug delivery system configured to be activated by a user, i.e., a patient or a subject, immediately prior to use. Electrodes of an exemplary self-contained co-packaged iontophoretic drug delivery system are protected from degradation from contact with a conducting medium or one or more therapeutic compounds. This may be beneficial, e.g., because it can result in an extended shelf life. The exemplary iontophoretic drug delivery system can be easily and reliably activated by a user. Further, the exemplary iontophoretic drug delivery system provides a controlled and accurate effective dose of a therapeutic drug to a user.

Iontophoretic patches according to the present invention have improved shelf-storage stability, reliability and ease of use, as compared to patches previously described in the prior art.

If a product that includes a drug is not stable under normal shelf storage conditions, it is unlikely to be a successfully commercialized product because the short shelf life limits the product's utility to most potential users as most of the product's useful life is exhausted during the time required for manufacturing and the distribution process. Thus, determination of shelf storage stability is an important part of a drug product's regulatory approval process. If there are difficulties with storage stability, regulatory approval may be withheld.

An electrode of an iontophoretic drug delivery system may chemically react with a therapeutic compound over time, leading to degradation of the therapeutic compound or the device itself. To prevent shelf storage stability problems, many of the iontophoretic drug delivery systems reported in the literature require that the therapeutic compound be stored separately from the electrodes until immediately prior to use. (See, e.g., U.S. Pat. No. 5,817,044). The device electrode (e.g., the electrode and the power controller) may be maintained in a dry (unhydrated) condition prior to use also because of the tendency of the active electrode material to undergo physical and chemical changes during shelf storage when in a hydrated state.

Storing several components of an iontophoretic drug delivery system separately decreases the ease of use of the device and introduces complexity, which may reduce the safety and the reliability of the device. There are regulatory requirements related to the accuracy and precision of content of a particular drug in an individual dosage form. Devices with separately stored components usually require that a user introduce the drug into a reservoir in contact with the electrode and hydrate the reservoir prior to use. Such operations that depend upon the user to load the drug into the device under relatively uncontrolled conditions may result in improper dosing.

Embodiments of the present invention include a self-contained co-packaged iontophoretic drug delivery system configured to be reliably and easily activated by, e.g. a patient, caregiver or a subject, prior to use. An exemplary drug delivery system sealingly separates an electrode from a conductive reservoir including a conductive medium prior to use. In some embodiments, exemplary drug delivery systems sealingly separate an electrode from a conductive reservoir including a conductive medium and a therapeutic compound prior to use. In some embodiments, exemplary drug delivery systems also sealingly separate an electrode from a conductive reservoir including a conductive medium and an ion source prior to use. The exemplary system is configured to be activated by a user while a first electrode, a second electrode, a power controller, a first conductive reservoir including a conductive medium and a therapeutic compound and a second conductive reservoir including a conductive medium and remain within a protective housing. In a further embodiment, the power controller comprises a microprocessor with appropriate code, e.g., a firmware code, to control the power level of the patch.

After the system is activated, the protective housing may be opened and the assembled self-contained iontophoretic drug delivery patch applied to a subject. An exemplary self-contained iontophoretic drug delivery system prevents degradation of the first electrode or the second electrode or both by preventing prolonged contact with the first conductive medium, the second conductive medium, an ion source and/or the therapeutic compound, thereby extending the shelf life of the system. During activation components of the iontophoretic drug delivery patch remain within the protective housing, which protects the user from the therapeutic compound, the electrodes and the power controller, and protects the therapeutic compound, the electrodes and the power controller from the user. An exemplary self-contained iontophoretic drug delivery patch only requires a user to pull on a barrier (and, in some embodiments, press on a top portion of the housing), to electrically contact the electrodes with the conductive reservoirs.

One advantage of the present invention is that unwanted contact between the user and the therapeutic compound, e.g., the drug, is minimized. Since the drug is encapsulated in the reservoir and the housing and is activated by removing the barrier (and, in some embodiments, pressing on a top portion of the housing), unwanted contact with the drug by the user is minimized. Furthermore, since the drug is preloaded into the reservoir the maximum dosage is predetermined to prevent overdosing.

Before describing exemplary embodiments of the present invention, some terms used in this specification are defined.

The term "therapeutic compound" includes any compound which is capable of being administered in a therapeutically effective amount to a subject transdermally or through the use of iontophoresis. As used here a therapeutic compound may be a drug or other biologically active agent. Examples of a therapeutic compounds include, but are not limited to an analgesic, anesthetic, anti-arthritis drug, anti-inflammatory drug, anti-migraine drug, cardiovascularly active drug, smoke cessation drug, hormone, non-steroidal anti-inflammatory agent, anti-hypertensive agent, analgesic agent, antidepressant, antibiotic, anti-cancer agent, local anesthetic, antiemetic, anti-infectant, contraceptive, anti-diabetic agent, steroid, anti-allergy agent, agents for smoking cessation, or anti-obesity agent. Examples of therapeutic compounds include, but are not limited to, nicotine, androgen, estrogen, testosterone, estradiol, nitroglycerin, clonidine, dexamethasone, wintergreen oil, tetracaine, lidocaine, fentanyl, sufentanil, alfentanil, progestrone, insulin, Vitamin A, Vitamin C, Vitamin E, prilocaine, bupivacaine, scopolamine, dihydroergotamine, and pharmaceutically acceptable salts thereof. In a further embodiment, the therapeutic agent is a triptan compound, e.g., sumatriptan, almotriptan, zolmitriptan, rizatriptan, naratriptan, or a combination thereof.

The term "shelf life" includes the period of time that the iontophoretic drug delivery system (loaded with the therapeutic compound) can rest unused in ambient temperature and moisture levels and still be used to perform its intended function, e.g., administer the therapeutic compound to treat a subject, without degradation of the compound or the device. "Shelf life" for a self-contained iontophoretic drug delivery system can be one month or longer (e.g. at least 3 months, at least 6 months, at least one year, at least eighteen months, at least two years, at least three years, at least four years, etc.) In some embodiments, the self-contained devices of the invention are stable for at least two years.

The terms "activate", "activates", "activated" or the like, as used, herein refers to the electrical connection of one or both electrodes to one or both reservoirs, e.g., by removal of a barrier from between the electrode and a reservoir. In some embodiments, removal of the barrier, by itself, electrically connects the electrode and reservoir. In some embodiments, the electrode and reservoir must also be manually contacted, e.g., by pressing down on the device, to obtain electrical connection. "Activation" does not refer to powering the device (e.g., by manually pushing a button and/or completing the circuit by applying to the skin), to initiate delivery of the therapeutic agent.

The term "subject" includes animals (e.g., mammals, e.g., cats, dogs, horses, pigs, cows, sheep, rodents, rabbits, squirrels, bears, and primates (e.g., chimpanzees, gorillas, and humans)) which may be treatable by the methods and devices of the invention.

The term "treated," "treating" or "treatment" includes therapeutic and/or prophylactic treatment. The treatment includes the diminishment, alleviation of at least one symptom, or complete eradication of a state or condition.

In a further embodiment, the therapeutic agent is a triptan compound and the state which is treated is a triptan compound responsive state, e.g., states which can be treated by the administration of a triptan compound. Triptan compound responsive states include almotriptan responsive states, zolmitriptan responsive states, rizatriptan responsive states, sumatriptan responsive states, and naratriptan responsive states. The term also includes migraines, familiar hemiplegic migraines (with and without aura), chronic paroxysmal headaches, cluster headaches, migraine headaches, basilar migraines, and atypical headaches accompanied by autonomic symptoms.

As used herein, the term "conductive reservoir" refers to a reservoir, e.g., which includes or otherwise holds a conductive medium (alone or in combination with one or more therapeutic compounds, ion sources and other materials). When used in reference to the embodiments and figures herein, conductive reservoir is meant to include both the reservoir and the conductive medium. The term "reservoir" refers to a compartment or pocket where the conductive medium is held. Additional elements, such as one or more ion sources and/or therapeutic compounds, may also be held by the reservoir. The reservoir itself may be conductive or non-conductive. In some embodiments, the reservoir is non-conductive. The conductive medium may be any of those described in more detail herein.

As used herein, the term "ion source" refers to a source of charged species. Such sources include, for example, salts, electrolytes and/or charged therapeutic compounds. Exemplary ion sources include sodium and potassium salts such as sodium chloride. Such charged species may, for example, be in an aqueous solution.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1B:
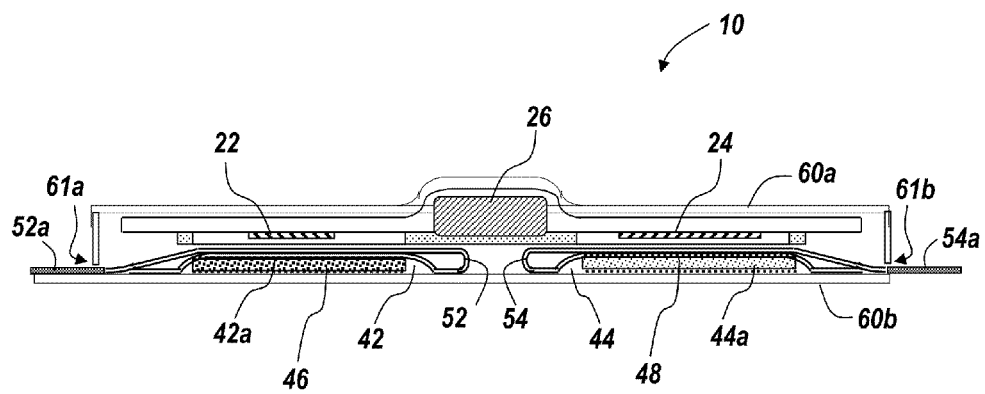
FIG. 1B illustrates a side view of the exemplary iontophoretic drug delivery system depicted in FIG. 1A.

FIGS. 1A and 1B illustrate an exemplary embodiment of a self-contained co-packaged iontophoretic drug delivery system 10 that is user-activated, in accordance with aspects of the present invention. In some embodiments, the device is activated upon removal of the removal barrier between the electrodes and the reservoirs. In other embodiments, the device is activated upon removal of the removal barrier and subsequent pressure placed upon the top portion of the protective housing (61a). The device then can be removed from the protective housing and applied to the body for delivery of the therapeutic agent. Some thicknesses in FIG. 1B are exaggerated for illustrative purposes. As depicted by the cross-sectional side view of FIG. 1B, the iontophoretic drug delivery system 10 includes a first electrode 22 and a second electrode 24, which may be a return electrode. In one embodiment of the invention, the electrodes 22 and 24 are round, circular, or coated wires. In a further embodiment the wires may be coated with zinc or silver (e.g., silver/silver chloride). In some embodiments, one electrode, e.g., the anode, is a zinc electrode and the other electrode, e.g., the cathode, is a silver/silver chloride electrode.

In another embodiment, the electrodes 22 and 24 further comprise a polyester film (29) such as biaxially-oriented polyethylene terephthalate polyester film, such as, Mylar® polyester film (DuPont) or AUTOSTAT CT3 polyester film (MacDermaid). Such films are advantageous material because of their thinness and flexibility. The electrodes may be screen-printed on such films with conductive ink comprising, e.g., silver/silver chloride. The films may further include a dielectric coating to provide electrical insulation.

In one embodiment, the electrode may be affixed to the body of the device and/or the subject using, e.g., an adhesive or other affixing means (32). In some embodiments, glue, over tape or fixing tape may be used to affix the electrode. In some embodiments, the adhesive or other affixing means is conductive. In other embodiments, the adhesive or other affixing means is non-conductive. Suitable adhesives include 1504 Transfer Adhesive available from 3M™. Additionally or alternatively, the electrode may be fixed in the device by sandwiching it between various layers and/or in an aperture or a concavity defined by a component, e.g., a backing layer and/or foam rings, configured to receive it and/or support it.

In a further embodiment, components may be affixed directly onto the polyester film. Examples of components include, but are not limited to, microprocessors and batteries. The components may be affixed with glue, solder, or tabs. The battery can be, e.g., one or two 3 volt coin cell lithium batteries.

The system also includes a power controller 26 configured to control a current flow between the first electrode 22 and the second electrode 24. The power controller may include a switch, such as a dome switch. A cover dome 25 can provide protection and insulation of the power controller. The power controller is "integrated" into the device and cannot be removed and reused, e.g., with other devices. In some embodiments, it is a single-use power controller that does not allow the user to re-power it after its proper use, e.g., to deliver any drug left in the device. The system further includes a first conductive reservoir 42 including a first conductive medium 42a and a therapeutic compound 46 and a second conductive reservoir 44 including a second conductive medium 44a, which may hold an ion source. In use, current supplied to the first electrode 22 drives the therapeutic compound 46 from the first conductive medium 42a into a portion of a patient in contact with the first conductive medium 42a. Current returns to the second electrode 24 through a portion of the patient in contact with the second conductive medium 44a. The second conductive reservoir 44 or the second conductive medium 44a may include a second therapeutic compound and/or ion source 48 having a charge opposite that of the therapeutic compound 46. Foam rings 34 shown in FIG. 2b may be used to hold the conductive media in place within the conductive reservoirs. The foam rings may further keep the anode and cathode of the electrode separated.

A removable barrier 52 forms a first barrier seal removably disposed between the first electrode 22 and the first conductive medium 42a. A second removable barrier 54 may form a second barrier seal removably disposed between the second electrode 24 and the second conductive medium 44a as depicted, according to aspects of the present invention. Alternatively, the removable barrier may form both the first barrier seal and a second barrier seal removably disposed between the second electrode 24 and the second conductive medium 44a. In one embodiment, the removable barrier comprises foil. As described above, prolonged contact between the first conductive medium 42a including the therapeutic compound 46 and the first electrode 22 may cause degradation of the first electrode 22, the therapeutic agent or both. The removable barrier 52, which forms the first barrier seal, prevents the first conductive medium 42a including the therapeutic compound 46 from coming into contact with the first electrode 22, thus preventing water transmission. By separating the first conductive medium 42a from the first electrode 22 with a sealed barrier ("sealingly separating") and sealingly separating the second conductive medium 44a from the second electrode 24, the iontophoretic drug delivery system 10 maintains efficacy and reliability, thus providing a longer shelf-life.

The system 10 also includes a housing (60a and 60b) to house the first electrode 22, the second electrode 24, the power controller 26, the first conductive reservoir 42 including a first conductive medium 42a and the second conductive reservoir 44 including a second conductive medium 44a. The housing has a top housing portion 60a that is coupleable to a bottom housing portion 60b. The top housing portion 60a and the bottom housing portion 60b are coupled to form a slotted sidewall portion 61a through which the removable barrier 52 extends. Similarly, the top housing portion 60a and the bottom housing portion 60b may form a second slotted sidewall portion 61b through which the second removable barrier 54 extends as depicted, according to aspects of the present invention. A portion of the removable barrier layer that extends outside the housing provides a user access to the removable barrier layer 52 (and/or the second removable barrier 54) without opening the housing. The removable bather 52 (and/or the second removable barrier 54) is configured to be removed while the first electrode 22, the second electrode 24, the power controller 26, the first conductive reservoir 42 including a first conductive medium 42a and the second conductive reservoir 44 including a second conductive medium 44a remain within the housing. The portion of the removable barrier 52 extending through the slotted sidewall portion 61a may be in the form of a first tab 52a. Likewise, a portion of the second removable barrier 54 extending through the second slotted sidewall portion 61b may be in the form of a second tab 54a. A user may remove the barrier layer 52 and the second barrier layer 54 by pulling on the first tab 52a and the second tab 54a without accessing the first electrode 22, the second electrode 24, the power controller 26, the first conductive reservoir 42 including a first conductive medium 42a and the second conductive reservoir 44 including a second conductive medium 44a, enabling assembly of a self-contained iontophoretic patch while components of the self-contained iontophoretic patch remain within the housing (60a and 60b).

Figure 2A:
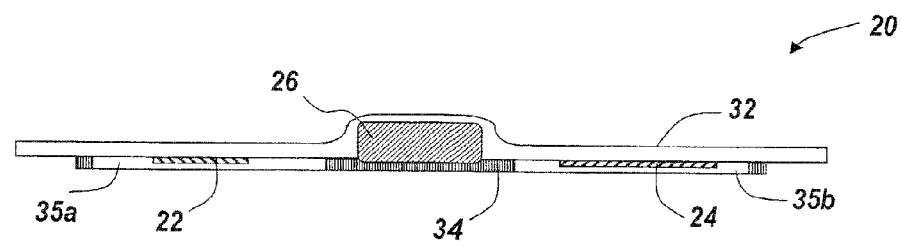
FIG. 2A illustrates a cross-sectional side view of a portion of an exemplary iontophoretic drug delivery system that includes a first electrode, a second electrode and a power controller, according to aspects of the present invention.
Figure 2B:
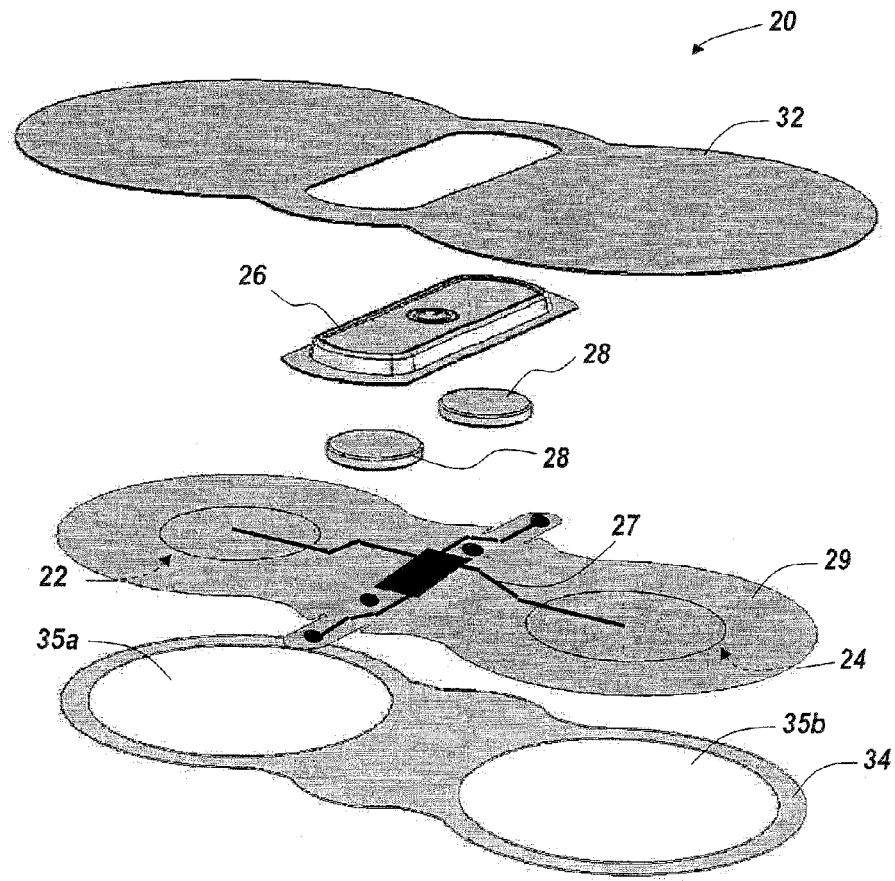
FIG. 2B illustrates an exploded perspective view of the portion depicted in FIG. 2A.

FIGS. 2A and 2B illustrate a portion of the exemplary self-contained iontophoretic drug delivery system 10 that includes the first electrode 22, the second electrode 24 and the power controller 26 which may be under a dome 25. In the side cross-sectional view depicted in FIG. 2A, some thicknesses are exaggerated for illustrative purposes. The first electrode 22 and the second electrode 24 may be described as an electrode region of the iontophoretic drug delivery system 10. The iontophoretic drug delivery system 10 may include at least one battery 28 for providing current to the power controller 26, the first electrode 22 and the second electrode 24. The power controller 26 may be electrically connected 27 to at least one battery 28, the first electrode 22 and the second electrode 24 with circuitry 27. The circuitry 27, the first electrode 22 and the second electrode 24 may be disposed on an electrode support layer (e.g., a polyester film) 29 as depicted, according to aspects of the present invention.

The power controller 26, the first electrode 22 and the second electrode 24 may be supported by a backing layer 32, according to aspects of the present invention. The electrode support layer 29 may be affixed to the backing layer 32. The iontophoretic drug delivery system 10 may also include a receiving layer 34 that has a first recess 35a configured to receive the first conductive reservoir 42 and a second recess configured to receive the second conductive reservoir 44. In a further embodiment, the backing comprises material such as, but not limited to cloth, gauze, plastic and rayon. In some embodiments, the backing is at least partially adhesive (e.g., the portion of the backing that contacts the skin of the user).

Figure 3A:
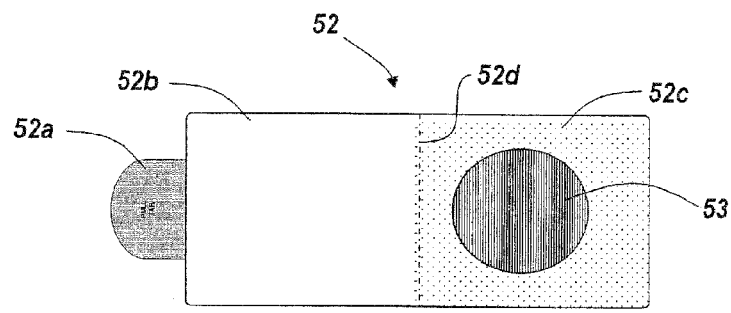
FIG. 3A illustrates a top view of an unfolded removable barrier, according to aspects of the present invention.

FIG. 3A illustrates a top planar view of the removable barrier 52 unfolded. The removable barrier 52 may include a tab portion 52a as described above. The removable barrier 52 may further include a liner portion 52b that faces the first electrode 22 and an impermeable portion 52c that faces the first conductive reservoir 42 including a first conductive medium 42a. The liner portion 52b and the impermeable portion 52c may be separated by a fold line 52d. A surface of the liner portion 52b that faces the first electrode 22 may have a low coefficient of friction enabling it to be removed with minimal frictional resistance. A surface of the impermeable portion 52c that faces the first conductive reservoir is impermeable to a conducting medium 42a and the therapeutic compound 46 in the first conductive reservoir 42. The removable bather 52 may also include a non-stick portion 53 that faces the first conductive reservoir 42 and first conductive medium 42a to minimize frictional force on the first conductive reservoir 42 when the removable barrier 52 is removed. In some embodiments, the entire removable barrier is an impermeable and non-stick barrier. In other embodiments, only portions of the removable barrier are impermeable and non-stick including but not limited to, e.g., those portions contacting the electrode and/or the reservoirs.

Figure 3B:
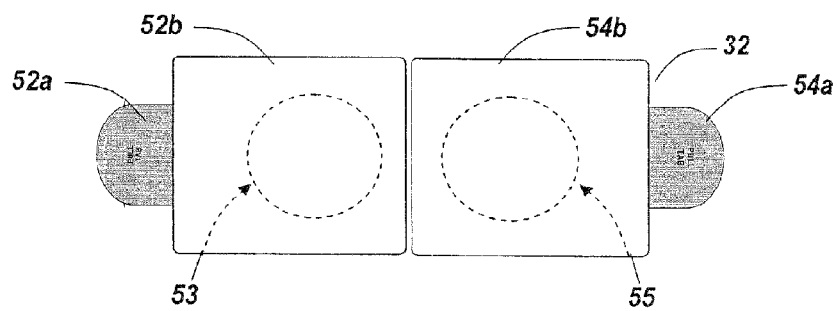
FIG. 3B illustrates a top view of a removable barrier and a second removable barrier, which are both folded, according to one aspect of the present invention.
Figure 3C:
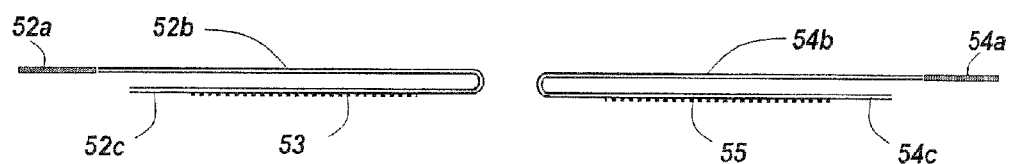
FIG. 3C illustrates a side view of the removable barrier and the second removable bather depicted in FIG. 3B.

FIGS. 3B and 3C illustrate the removable barrier 52 folded along the fold line 52d (depicted in FIG. 3A) and the folded second removable bather 54. Some thicknesses in FIG. 3C are exaggerated for illustrative purposes. Like the removable barrier 52, the second removable barrier 54 may include a tab portion 54a for accessing the second barrier 54 from outside the housing (60a and 60b) as described above. Similarly, the second removable barrier 54 may include a liner portion 54b with a surface facing the second electrode 24 that has a low coefficient of friction and may include an impermeable portion 54c with a surface facing the second conductive reservoir 44 including a second conductive medium 44a that is impermeable to a second conducting medium 44a. The second removable barrier 54 may also include a non-stick portion 55 that faces the second conductive reservoir 44 and second conductive medium 44a.

Figure 4A:
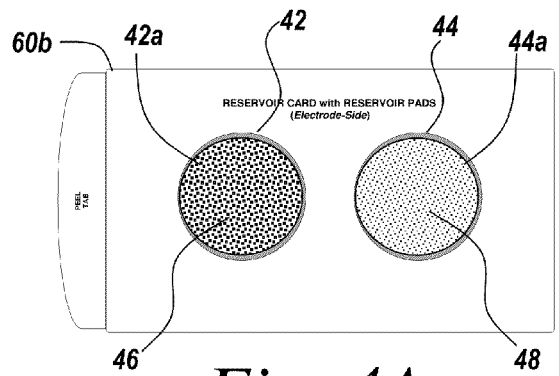
FIG. 4A depicts a top planar view of a bottom housing portion supporting a first conductive reservoir and a second conductive reservoir, according to aspects of the present invention.

FIG. 4A illustrates a top planar view of the bottom housing portion 60b supporting the first conductive reservoir 42 including a first conductive medium 42a and second conductive reservoir 44 including a second conductive medium 44a, according to aspects of the present invention. The first conductive reservoir 42 includes a first conducting medium 42a, e.g., a non-woven pad such as rayon, and holds a therapeutic compound 46. The therapeutic compound may, for example, be dispersed within the non-woven pad, e.g., in an aqueous solution. The second conductive reservoir 44 includes a second conducting medium 44a, e.g., a non-woven pad such as rayon, and may also hold a second therapeutic compound 48, according to aspects of the present invention.

The term "triptan compound" includes triptan compounds, derivatives and salts. The term also includes compounds that contain a 2-(1H-indol-3-yl)-N,N-dimethylethanamine moiety. Examples of triptan compounds include, but are not limited to, almotriptan, frovatriptan, eletriptan, zolmitriptan, rizatriptan, sumatriptan, naratriptan, and pharmaceutically acceptable salts thereof.

Examples of pharmaceutically acceptable salts of triptan compounds which may be used in the embodiments of the invention include, but are not limited to, chloride, bromide, iodide, sulfuric, phosphate, lactate, citrate, tartarate, salicylate, succinate, maleate, gluconate, mesylate, laurate, dodecylate, myristate, palmitate, stearate, coconoate, behinate, oleate, linoleate, linolenate, eicosapentaenoate, eicosahexaenoate, docosapentaenoate, docosahexaenoate, eicosanoids and the like. In a further embodiment, the triptan compound is sumatriptan succinate. In certain embodiments, the salt of the triptan compound may be selected such that it does not react with the other components of the patch, such as the metal electrode. In certain embodiments, the salt may be selected such that it does not form a significant amount of an insoluble residue when in contact with the metal components of the patch of the invention.

The first conductive reservoir 42 and/or the second conductive reservoir 44 may include, e.g., dispersed within a non-woven pad as a conductive medium or otherwise contained within the reservoir, a hydrogel and/or a polyamine, according to aspects of an exemplary embodiment. Accordingly, the first conducting medium 42a and/or the second conducting medium 44a may be a hydrogel. The term "hydrogel" includes materials which comprise polymer chains that are soluble. Examples of such polymers that the hydrogel may be based upon include polyacrylates, polyisobutylene, polyisoprene, styrene-polybutylene-styrene block copolymers, polysiloxanes, polyurethanes, and combinations thereof. The hydrogel may be in the form of one or more colloidal gels. Examples of hydrogels include, but are not limited to a gum, alginate, alkyl or hydroxyalkylalkylcellulose, carboxymethylcellulose, gum agar, hydroxethylcellulose, hydroxypropyl methyl cellulose (HPMC), locust bean gum, pectins, polyacrylamide, polyethylene glycol, poly(ethylene oxide), poly(propylene oxide), polyvinyl alcohol, polyvinylpyrrolidine (PVP), poly(acrylic acid) and combinations thereof. The hydrogel may also include an aqueous medium. The aqueous medium may be selected such that it does not interfere with the ionic transport of the compounds of the invention and/or such that it has a high ionic conductivity.

The first conductive reservoir 42 may include a polyamine as a conductive medium. For example, in some embodiments, the first conductive reservoir includes a polyamine as a conductive medium loaded onto a non-woven pad. The term "polyamine" particularly includes cationic organic compounds having at least two positively charged groups, preferably amino groups selected from the group comprising primary amino groups, secondary amino groups and tertiary amino groups. The invention also includes polyamines comprising, for instance, pyrrolidino, piperidino or morpholino groups. Generally, the polyamines used in accordance with the present invention preferably include polyelectrolytes which are polymers or macromolecules comprising two or more positive charges upon being dissolved in water or an aqueous solvent.

In a further embodiment, the term "polyamine" includes organic compounds having two or more primary amino groups. Examples include putrescine, cadaverine, spermidine, and spermine Other polyamines include cyclen and other cyclic polyamines. Examples of polymer polyamines include those based on the aziridine monomer, such as polyethylene amine.

According to one embodiment of the invention, the polyamine may selected from the group comprising acrylate copolymers, methacrylate copolymers, alkylated acrylate copolymers and alkylated methacrylate copolymers. These copolymers contain two or more amino groups as defined above.

In some embodiments, the first conductive reservoir 42 includes a therapeutic compound 46. The first conductive reservoir 42 may hold a solution that contains the therapeutic compound 46. The solution may be a conductive medium 42a. In some embodiments, the solution is a conductive medium loaded onto a non-woven pad. The term "solution" includes both aqueous solutions of the therapeutic compound 46 and solutions of the therapeutic compound 46 which comprise organic solvents. The solvent should be compatible with the therapeutic compound 46, the first conductive reservoir, and the technique of iontophoresis. Examples of solutions for use in the present invention include those compatible with a hydrogel and/or comprise a polyamide and those which are capable of being used for iontophoresis to deliver the compound to the subject.

Figure 4B:
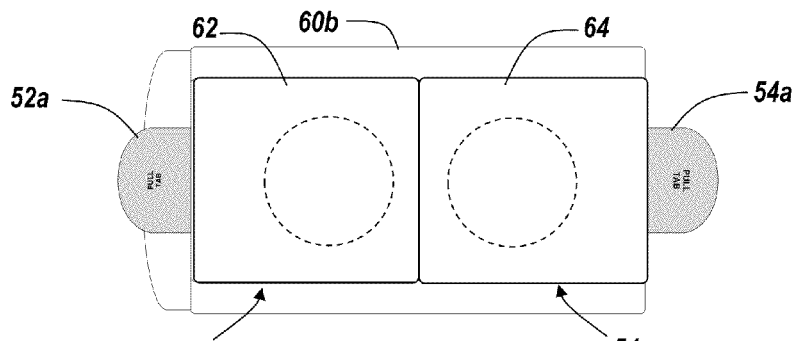
FIG. 4B illustrates a top view of the bottom housing portion depicted in FIG. 3A with a removable barrier covering the first conductive reservoir including a first conductive medium and a second removable barrier covering the second conductive reservoir including a second conductive medium, according to aspects of the present invention.
Figure 4C:
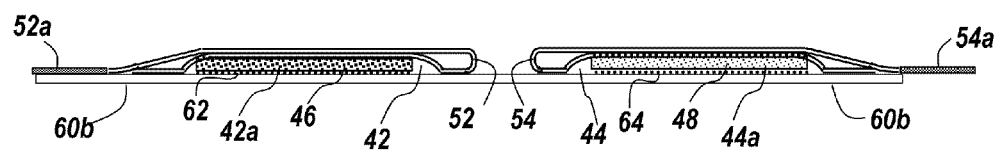
FIG. 4C illustrates a side view of the bottom housing portion, the first conductive reservoir including a first conductive medium and the second conductive reservoir including a second conductive medium depicted in FIG. 4B.

FIG. 4B and FIG. 4C illustrate the bottom housing portion 60b depicted in FIG. 4A with a removable bather 52 covering the first conductive reservoir 42 including a first conductive medium 42a and a second removable barrier 54 covering the second conductive reservoir 44 including a second conductive medium 44a, according to aspects of the present invention. The bottom housing portion 60b may include a first nonstick portion 62 in contact with the first conductive medium 42a and a second nonstick portion 64 in contact with the second conductive medium 44a, as depicted in the side cross-sectional view of FIG. 4C.

Figure 5A:
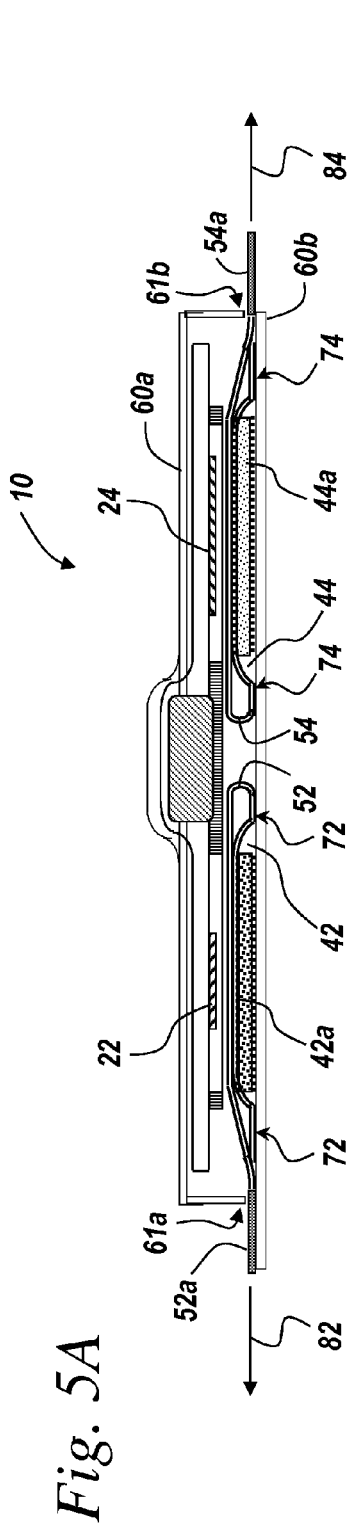
FIG. 5A illustrates a side cross-sectional view of an initial state of the exemplary drug delivery system.

FIGS. 5A through 5F illustrate the exemplary self-contained co-packaged iontophoretic drug delivery system 10 in use. As depicted in FIG. 5A, initially, the first electrode 22 is separated from the first conductive reservoir 42 including a first conductive medium 42a by the removable bather 52 which forms a first barrier seal 72. The first conductive reservoir 42 and the first conductive medium 42a may be sealed between the removable bather 52 and the bottom housing portion 60b as shown, according to aspects of an exemplary embodiment. The second electrode 24 is separated from the second conductive reservoir 44 including a second conductive medium 44a by a second removable barrier 54 which forms a second barrier seal 74. The first barrier seal 72 and the second barrier seal 74 prolong the shelf life of the iontophoretic drug delivery system 10 by preventing degradation of the first electrode 22, the second electrode 24 and the therapeutic compound 46 due to contact between the electrodes and the conductive media. A user may begin activation of the system by simultaneously (or substantially simultaneously) pulling on both the tab portion 52a of the removable barrier as indicated by arrow 82, and the tab portion 52b of the second removable barrier as indicated by arrow 84.

Figure 5B:
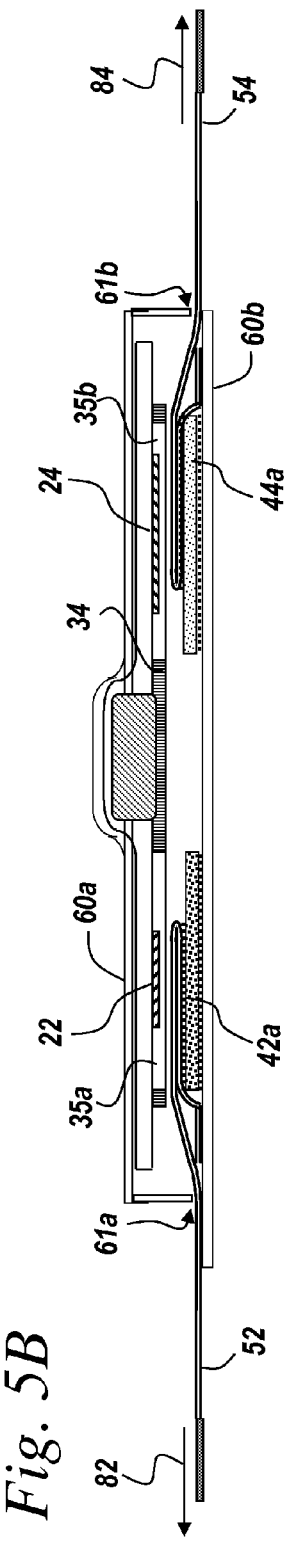
FIG. 5B illustrates a side cross-sectional view of the exemplary drug delivery system showing forces applied to remove a removable barrier and a second removable barrier.
Figure 5C:
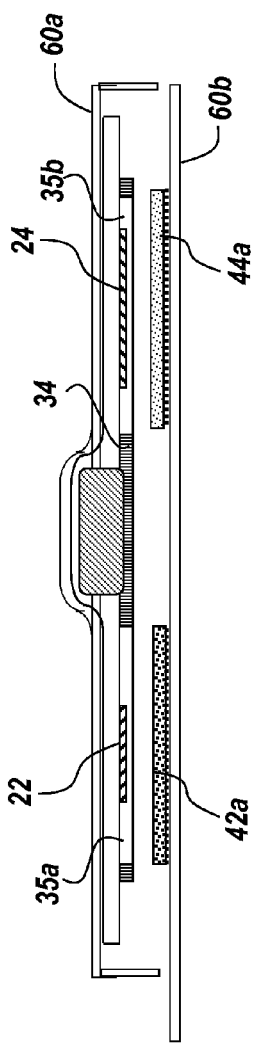
FIG. 5C illustrates a side cross-sectional view of the exemplary drug delivery system after the removable barrier and the second removable barrier have been removed.

FIG. 5B illustrates the iontophoretic drug delivery system as the removable barrier 52 is being pulled out of the housing (60a and 60b) through the slotted sidewall portion 61a breaching the first barrier seal 72 and exposing the first conductive reservoir 42 and the first conductive medium 42a. Consecutively, concurrently, or simultaneously, the second removable barrier 54 is being pulled out of the housing (60a and 60b) through the second slotted sidewall portion 61b breaching the second bather seal 74 and exposing the second conductive reservoir 44 and the second conductive medium 44a. FIG. 5C illustrates the iontophoretic drug delivery system 10 after removal of both the removable bather 52 and the second removable barrier 54 with the first electrode 22 facing the first conductive medium 42a and the second electrode 24 facing the second conductive medium 44a. As shown, the first recess 35a of the receiving layer 34 is configured to receive the first conductive medium 42a and the second recess 35b of the receiving layer 34 is configured to receive the second conductive medium 44a. In FIG. 5C, there is a space between the receiving layer 34 and the first conductive medium 42a and between the receiving layer 34 and the second conductive medium 44a after the removal of the removable barrier 52 and the second removable barrier 54 for illustrative purposes. Forces exerted on the receiving layer 34 when the removable barrier 52 and the second removable barrier 54 are removed may bring the receiving layer 34 into contact with the first conductive medium 42a (e.g., a layer comprising the first conductive medium) and the second conductive medium 44a (e.g., a layer comprising the second conductive medium). In some embodiments, the receiving layer is a foam ring.

Figure 5D:
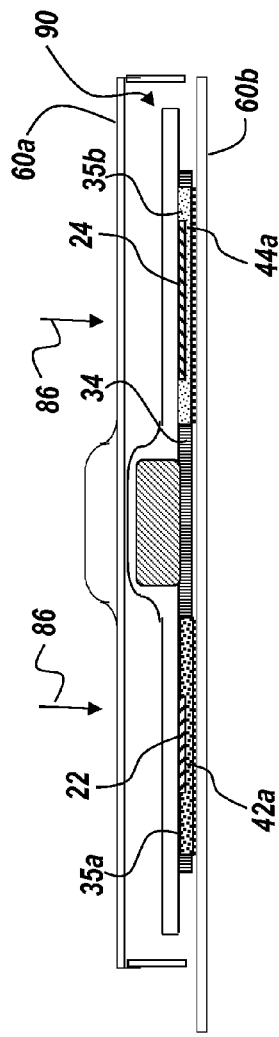
FIG. 5D illustrates a side cross-sectional view of the exemplary drug delivery system with the first electrode in contact with the first conductive medium and with the second electrode in contact with the second conductive medium after a user applied force to a top housing portion.

In FIG. 5D, a force is exerted on the top housing portion 60a as indicated by arrows 86 to cause physical and electrical contact between the first electrode 22 and the first conductive medium 42a and the second electrode 24 and the second conductive medium 44a. In some embodiments, force may also or instead be exerted on the bottom housing portion 60b, in order to produce electrical contact between the first electrode 22 and the first conductive medium 42a and the second electrode 24 and the second conductive medium 44b. The top housing portion 60a may be deformable under the force 86 to exert downward pressure on the backing layer 32. The first conductive medium 42a held thereby may adhere to the first electrode 22 due to material properties of the first conductive medium 42a, the therapeutic compound 46 or both. Alternatively, the first conductive medium 42a and/or the first electrode 22 may have a layer of adhesive, e.g., electrically conductive adhesive or electrically non-conductive adhesive, to adhere the first conductive medium 42a to the first electrode 22. Likewise the second conductive medium 44a may have material properties which cause it to adhere to the second electrode 24, or an adhesive, e.g., electrically conductive adhesive or electrically non-conductive adhesive, may affix the second conductive medium 44a to the second electrode 24. Examples of adhesives that may be used to adhere the first conductive medium to the first electrode and/or the second conductive medium to the second electrode include transfer rings which utilize material that aids in affixing the medium to the electrode. In some embodiments, one or more of the adhesives utilized is a pressure sensitive adhesive. The adherence of the first conductive medium to the first electrode and/or the adherence of the second conductive medium to the second electrode may occur due to the deformation of the top housing as described above.

Additionally, or alternatively, the reservoirs and electrodes may be electrically connected by contact and this contact may be affected and/or maintained by the configuration of the device that effects and/or maintains their physical proximity. After the first conductive medium 42a adheres or otherwise connects to the first electrode 22 and the second conductive medium 44a adheres or otherwise connects to the second electrode 24, the first electrode 22, the second electrode 24, the power controller 26, the first conductive medium 42a, second conductive medium 44a, and optionally at least one battery 28, the electrode support layer 29, the circuitry 27 and the backing layer 32, the self-contained iontophoretic drug delivery patch 90 is activated and ready for application and actuation of the power controller by the user, e.g., via a push button. The electrodes and reservoirs are protected and stabilized during application and use, in part, by the backing layer 32 and the receiving layer 34.

Figure 5E:
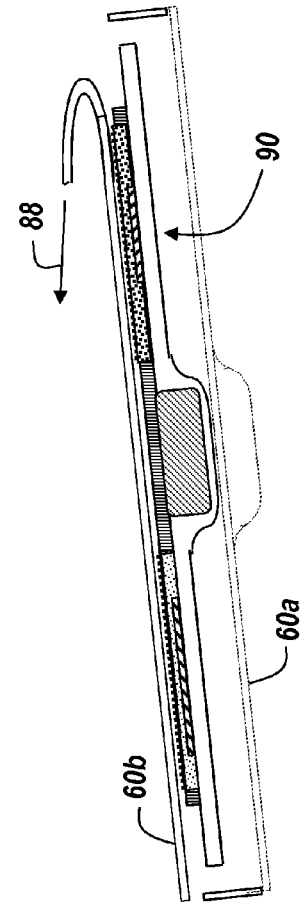
FIG. 5E illustrates a side cross-sectional view of the exemplary drug delivery system as the bottom housing portion is removed to access the activated self-contained drug delivery patch.
Figure 5F:
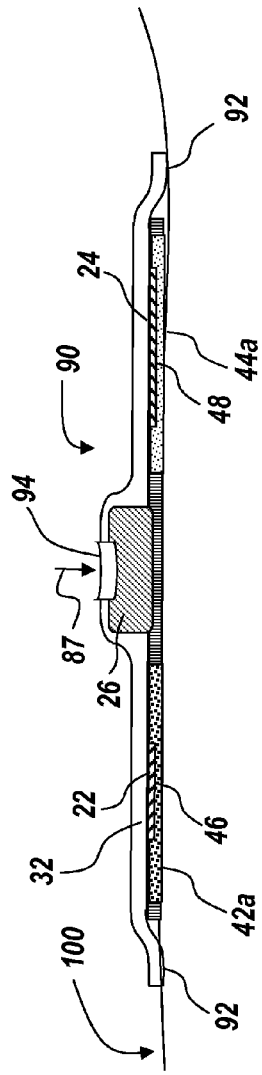
FIG. 5F illustrates a side cross-sectional view of the activated self-contained drug delivery patch applied to a subject's skin.

The bottom housing portion 60b may be peeled away indicated by arrow 88 to access to the self-contained iontophoretic drug delivery patch 90, as illustrated by FIG. 5E. The self-contained iontophoretic drug delivery patch 90 may be removed from top housing portion 60a and applied to a subject 100. Optionally, the iontophoretic drug delivery patch 90 may be first removed from the top housing portion 60a, then subsequently peeled away from the bottom housing 60b.

The self-contained iontophoretic drug delivery patch 90 is applied to a subject's 100 skin. According to aspects of an illustrative embodiment, the backing layer 32 may have an adhesive surface 92 allowing the layer 32 to adhere to the subject's skin and securing the self-contained iontophoretic drug delivery patch 90 in place. The self-contained iontophoretic drug delivery patch 90 may also include a button 94 for electrically actuating the power controller 26. After the self-contained iontophoretic drug delivery patch 90 is secured a user may electrically actuate the power controller by pushing the button as indicated by arrow 87. Alternatively, the power controller 26 may be electrically actuated by another mechanical means. In some embodiments, the power controller 26 may become active due to electrical contact with the subject. After the self-contained iontophoretic drug delivery patch 90 is adhered to the subject 100 and actuated, the power controller 26 supplies current to the first electrode 22 and the second electrode 24 to drive the therapeutic compound 46, and optionally a second therapeutic compound 48, into the subject to deliver a therapeutically effective amount of one or both.

The polarity of the first electrode 22 is determined by the charge of the therapeutic compound 46. If the therapeutic compound 46 is positively charged then the first electrode 22 may be held at a positive current, relative to the second electrode 24, to drive the positively charged therapeutic compound 46 away from the first electrode 22 out of the first conductive medium 42a and into the subject 100. If the therapeutic compound 46 is negatively charged then the first electrode 22 may be held at a negative current, relative to the second electrode 24, to drive the negatively charged therapeutic compound 46 away from the first electrode 22 and into the subject 100.

The second conductive reservoir 44 allows current to return to the second electrode 24 through the second conductive medium 44a. The second conductive reservoir 44 may also hold a second therapeutic compound 48 with a charge opposite that of the therapeutic compound 46 in the first conductive reservoir 42 allowing for simultaneous delivery of a therapeutic compound with a positive charge and a therapeutic compound with a negative charge.

In another aspect, the invention provides methods of delivering a therapeutic compound, e.g., sumatriptan succinate, employing any of the drug delivery systems described herein to deliver a therapeutic agent to a subject. In one embodiment, the method generally includes applying an activated device to a subject.

The device may be applied to any appropriate surface of the subject. In some embodiments, the device is applied to the upper arm, leg (e.g., thigh), or back (e.g., upper back). In some embodiments the device is worn for a prescribed period of time, e.g., about 1, 2, 3, 4, 5, 6, 7, 8, 9, 10 or more hours. For example, in one embodiment, the device includes sumatriptan succinate and is applied to the upper arm or back for about 4 or for about 5 hours.

One skilled in the art will appreciate further features and advantages of the invention based on the above-described embodiments. Accordingly, the invention is not to be limited by what has been particularly shown and described, except as indicated by the appended claims.

EQUIVALENTS

While the systems, devices and methods of the present invention have been particularly shown and described with reference to the exemplary embodiments thereof, those of ordinary skill in the art will understand that various changes may be made in the form and details herein without departing from the spirit and scope of the present invention. Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate systems, devices, components, processes, and methods of those patents, applications and other documents may be selected for the present invention and embodiments thereof.

The invention claimed is:

1. A self-contained co-packaged single-use iontophoretic drug delivery system comprising:
   a first electrode;
   a second electrode;
   an integrated power controller in electrical connection with the first and second electrodes;
   circuitry connecting the first electrode and the second electrode with the integrated power controller;
   a first conductive reservoir aligned with the first electrode, the first conductive reservoir comprising a first conductive medium and a therapeutic compound;
   a second conductive reservoir aligned with the second electrode, the second conductive reservoir comprising a second conductive medium;
   a removable barrier forming a first barrier seal removably disposed between the first electrode and the first conductive reservoir, wherein the first conductive reservoir comprises the first conductive medium and the therapeutic compound while the first barrier seal remains intact, and wherein the first conductive medium and the first electrode are configured to adhere to each other forming electrical contact only after removal of the removable barrier;
   a second removable barrier forming a second barrier seal removably disposed between the second electrode and the second conductive reservoir, wherein the second conductive medium and the second electrode are configured to adhere to each other forming electrical contact only after removal of the second removable barrier layer;
   a first transfer ring configured to affix the first conductive medium to the first electrode after removal of the removable barrier and to maintain a position of the first conductive medium relative to the first electrode during use;
   a second transfer ring configured to affix the second conductive medium to the second electrode after removal of the second removable barrier and to maintain a position of the second conductive medium relative to the second electrode during use; and
   a removable protective housing which supports the first electrode, the first conductive reservoir, the second electrode, the second conductive reservoir and the power controller, the housing comprising a top housing portion coupled to a bottom housing portion; wherein a portion of the removable barrier extends outside the housing.

2. The iontophoretic drug delivery system of claim 1, wherein the removable barrier is configured to be removed while the first electrode, the second electrode, the power controller, the first conductive reservoir and the second conductive reservoir remain within the housing.

3. The iontophoretic drug delivery system of claim 1, wherein the top housing portion is deformable and configured to cause the first conductive medium to contact the first electrode when force is exerted on the top housing portion, the bottom housing portion or both after the removable barrier is removed.

4. The iontophoretic drug delivery system of claim 1, further comprising at least one battery disposed within the housing for supplying current to the first electrode and the second electrode.

5. The iontophoretic drug delivery system of claim 1, further comprising a support layer for supporting the power controller, the first electrode and the second electrode.

6. The iontophoretic drug delivery system of claim 1, further comprising a receiving layer having a first recess for receiving the first conductive medium and a second recess for receiving the second conductive medium.

7. The iontophoretic drug delivery system of claim 1, wherein the removable barrier has at least one non-stick portion for contacting the first conductive medium.

8. The iontophoretic drug delivery system of claim 1, wherein a portion of the removable barrier extending outside the housing comprises a tab.

9. The iontophoretic drug delivery system of claim 1, wherein the first conductive medium comprises a hydrogel.

10. The iontophoretic drug delivery system of claim 1, wherein the first conductive medium comprises a polyamide.

11. The iontophoretic drug delivery system of claim 1, wherein the therapeutic compound comprises a triptan compound.

12. The iontophoretic drug delivery system of claim 11, wherein triptan compound is sumatriptan.

13. The iontophoretic drug delivery system of claim 1, wherein the bottom housing portion supports the first conductive reservoir and the second conductive reservoir.

14. A method of treating a subject comprising administering to a subject a drug using the iontophoretic drug delivery system of claim 1.

15. A method for treating a triptan responsive state comprising administering to a subject an effective amount of a triptan compound using the iontophoretic drug delivery system of claim 11.

16. A method for treating a triptan responsive state comprising administering to a subject an effective amount of sumatriptan using the iontophoretic drug delivery system of claim 12.

17. A self-contained co-packaged iontophoretic drug delivery system comprising:
  an electrode region, comprising:
    a first electrode; and
    a second electrode;
  a power controller for controlling current supplied to the first electrode and the second electrode;
  circuitry connecting the first electrode and the second electrode with the power controller;
  a therapeutic compound region, comprising:
    a first conductive medium vertically aligned with the first electrode;
    a second conductive medium vertically aligned with the second electrode; and
    a therapeutic compound in solution disposed in the first conductive medium;
  a protective housing substantially enclosing the electrode region, the power controller region, the circuitry and the therapeutic compound region;
  a removable barrier layer separating a portion of the electrode region from a portion of the therapeutic compound region, the removable barrier layer having a portion accessible from outside the housing; and
  wherein the removable barrier layer is configured to be removed while the electrode region, the power controller, the circuitry and the therapeutic compound remain within the housing; and
  wherein upon removal of the barrier layer, the first conductive medium adheres to the first electrode and makes electrical contact therewith, and the second conductive medium adheres to the second electrode and makes electrical contact therewith;
  a first transfer ring configured to maintain a position of the first conductive medium relative to the first electrode during use; and
  a second transfer ring configured to maintain a position of the second conductive medium relative to the second electrode during use.

18. A method of treating a subject comprising administering to a subject a drug using the iontophoretic drug delivery system of claim 17.

* * * * *